(12) United States Patent
Young

(10) Patent No.: US 10,596,028 B2
(45) Date of Patent: *Mar. 24, 2020

(54) SELF-HEATED CONSUMER SPA PRODUCTS AND APPLICATIONS THEREOF

(71) Applicant: Forever Young International, Inc., Henderson, NV (US)

(72) Inventor: Daniel L. Young, Henderson, NV (US)

(73) Assignee: Forever Young International, Inc., Las Vegas, NV (US)

(*) Notice: Subject to any disclaimer, the term of this patent is extended or adjusted under 35 U.S.C. 154(b) by 117 days.

This patent is subject to a terminal disclaimer.

(21) Appl. No.: 15/648,331

(22) Filed: Jul. 12, 2017

(65) Prior Publication Data

US 2017/0304111 A1 Oct. 26, 2017

Related U.S. Application Data

(63) Continuation of application No. 13/387,247, filed as application No. PCT/US2010/043230 on Jul. 26, 2010, now Pat. No. 9,730,832.

(Continued)

(51) Int. Cl.
*A61F 7/03* (2006.01)
*A61H 7/00* (2006.01)
(Continued)

(52) U.S. Cl.
CPC ............... *A61F 7/034* (2013.01); *A61F 7/03* (2013.01); *A61H 7/002* (2013.01); *A61H 15/0092* (2013.01); *A61H 15/02* (2013.01); *A61H 36/00* (2013.01); *B32B 1/00* (2013.01); *B32B 5/024* (2013.01); *B32B 5/26* (2013.01); *B32B 7/14* (2013.01); *B32B 15/14* (2013.01); *B32B 27/12* (2013.01); *B32B 27/32* (2013.01); *B32B 29/02* (2013.01); *A61F 2007/0002* (2013.01); *A61F 2007/0036* (2013.01); *A61F 2007/0045* (2013.01); *A61F 2007/0217* (2013.01);
(Continued)

(58) Field of Classification Search
CPC combination set(s) only.
See application file for complete search history.

(56) References Cited

U.S. PATENT DOCUMENTS 622,350 A 4/1899 Hans
1,270,635 A 6/1918 Ljungstrom
(Continued)

FOREIGN PATENT DOCUMENTS

JP H04364848 A 12/1992
JP 670735 U 10/1994
(Continued)

OTHER PUBLICATIONS

International Bureau, International Search Report for International Application No. PCT/US2010/043230, dated Feb. 10, 2011, pp. 1-2, Geneva, Switzerland.
(Continued)

*Primary Examiner* — Kaitlyn E Smith
(74) *Attorney, Agent, or Firm* — Rimon, P.C.

(57) ABSTRACT

The following description relates generally to self-heated consumer spa products heated by means of a prolonged exothermic chemical reaction for various therapeutic and/or spa applications for applying heat to portions of a person's body.

13 Claims, 12 Drawing Sheets

Related U.S. Application Data

(60) Provisional application No. 61/228,590, filed on Jul. 26, 2009, provisional application No. 61/228,595, filed on Jul. 26, 2009, provisional application No. 61/228,593, filed on Jul. 26, 2009, provisional application No. 61/228,596, filed on Jul. 26, 2009.

(51) Int. Cl.

| | | |
|---|---|---|
| *A61H 15/00* | (2006.01) | |
| *A61H 15/02* | (2006.01) | |
| *A61F 7/00* | (2006.01) | |
| *A61F 7/02* | (2006.01) | |
| *A61H 36/00* | (2006.01) | |
| *B32B 5/02* | (2006.01) | |
| *B32B 5/26* | (2006.01) | |
| *B32B 7/14* | (2006.01) | |
| *B32B 15/14* | (2006.01) | |
| *B32B 27/12* | (2006.01) | |
| *B32B 27/32* | (2006.01) | |
| *B32B 29/02* | (2006.01) | |
| *B32B 1/00* | (2006.01) | |
| *A61N 5/06* | (2006.01) | |
| *A61H 33/06* | (2006.01) | |

(52) U.S. Cl.
CPC .............. *A61F 2007/0219* (2013.01); *A61F 2007/0257* (2013.01); *A61F 2007/0258* (2013.01); *A61H 7/003* (2013.01); *A61H 33/06* (2013.01); *A61H 2015/0014* (2013.01); *A61H 2033/061* (2013.01); *A61H 2201/0111* (2013.01); *A61H 2201/0153* (2013.01); *A61H 2201/0207* (2013.01); *A61H 2201/0257* (2013.01); *A61H 2201/0278* (2013.01); *A61H 2201/10* (2013.01); *A61H 2201/1253* (2013.01); *A61H 2201/164* (2013.01); *A61H 2201/1604* (2013.01); *A61H 2201/165* (2013.01); *A61H 2201/168* (2013.01); *A61H 2201/1635* (2013.01); *A61H 2201/1654* (2013.01); *A61H 2201/1664* (2013.01); *A61H 2201/1671* (2013.01); *A61H 2201/1685* (2013.01); *A61H 2205/02* (2013.01); *A61H 2205/06* (2013.01); *A61H 2205/10* (2013.01); *A61N 2005/0668* (2013.01); *B32B 2255/24* (2013.01); *B32B 2262/0253* (2013.01); *B32B 2262/06* (2013.01); *B32B 2307/30* (2013.01); *B32B 2307/7166* (2013.01); *B32B 2307/726* (2013.01); *B32B 2307/7265* (2013.01); *B32B 2307/748* (2013.01); *B32B 2437/00* (2013.01); *B32B 2437/02* (2013.01); *B32B 2555/00* (2013.01)

(56) References Cited

U.S. PATENT DOCUMENTS

| | | | |
|---|---|---|---|
| 1,380,986 A | 6/1921 | Linden | |
| 4,366,804 A | 1/1983 | Abe | |
| 5,455,970 A | 10/1995 | Vance et al. | |
| 5,456,704 A | 10/1995 | Kilcullen | |
| 5,597,577 A | 1/1997 | Mathewson | |
| 5,709,089 A | 1/1998 | Dawson et al. | |
| 5,736,110 A | 4/1998 | Angelillo et al. | |
| 5,776,177 A | 7/1998 | MacWhinnie et al. | |
| 5,792,213 A | 8/1998 | Bowen | |
| 5,915,461 A | 6/1999 | Tanhehco | |
| 5,967,308 A | 10/1999 | Bowen | |
| 6,019,782 A | 2/2000 | Davis et al. | |
| 6,116,231 A * | 9/2000 | Sabin | A61F 7/03 126/263.01 |
| 6,248,125 B1 | 6/2001 | Helming | |
| 6,269,654 B1 | 8/2001 | Murray et al. | |
| 6,289,889 B1 | 9/2001 | Bell et al. | |
| 6,409,746 B1 | 6/2002 | Igaki et al. | |
| 6,419,650 B1 | 7/2002 | Ryan et al. | |
| 6,511,446 B1 * | 1/2003 | Wu | A61F 7/02 601/15 |
| 6,524,331 B1 | 2/2003 | Kohout et al. | |
| 6,554,787 B1 * | 4/2003 | Griffin | A61F 7/02 601/70 |
| 6,648,904 B2 | 11/2003 | Altshuler et al. | |
| 6,666,850 B1 | 12/2003 | Ahr et al. | |
| 6,878,157 B1 | 4/2005 | Walters | |
| 6,886,553 B2 | 5/2005 | Yim | |
| 6,974,470 B2 | 12/2005 | Tsunakawa et al. | |
| 7,255,506 B2 | 8/2007 | Gruenbacher et al. | |
| 9,730,832 B2 * | 8/2017 | Young | A61F 7/034 |
| 10,188,549 B2 * | 1/2019 | Young | A61F 7/03 |
| 2001/0049546 A1 | 12/2001 | Dvoretzky et al. | |
| 2002/0017310 A1 | 2/2002 | Gruenbacher et al. | |
| 2002/0174863 A1 | 11/2002 | Saric et al. | |
| 2003/0041854 A1 * | 3/2003 | Sabin | A61F 7/034 126/263.01 |
| 2003/0083722 A1 | 5/2003 | Cordani et al. | |
| 2003/0100936 A1 | 5/2003 | Altshuler et al. | |
| 2003/0118779 A1 | 6/2003 | Fish et al. | |
| 2003/0195598 A1 | 10/2003 | Diroma et al. | |
| 2004/0055076 A1 * | 3/2004 | Yoo | A61F 7/02 2/338 |
| 2004/0065315 A1 | 4/2004 | Fish et al. | |
| 2005/0228465 A1 | 10/2005 | Harris et al. | |
| 2005/0228466 A1 | 10/2005 | Harris | |
| 2005/0283212 A1 | 12/2005 | Caceres et al. | |
| 2006/0018953 A1 | 1/2006 | Guillon et al. | |
| 2006/0258962 A1 | 11/2006 | Kopanic et al. | |
| 2007/0032751 A1 | 2/2007 | Roman | |
| 2007/0106356 A1 | 5/2007 | Carstens | |
| 2007/0142882 A1 | 6/2007 | Quincy et al. | |
| 2007/0156213 A1 | 7/2007 | Friedensohn et al. | |
| 2007/0256677 A1 | 11/2007 | Yim et al. | |
| 2009/0062890 A1 | 3/2009 | Ugajin et al. | |
| 2009/0149925 A1 | 6/2009 | MacDonald et al. | |
| 2009/0163984 A1 * | 6/2009 | Robinson | A61F 7/02 607/114 |
| 2009/0280043 A1 | 11/2009 | Ferguson | |
| 2009/0326619 A1 | 12/2009 | Kagan | |
| 2012/0265108 A1 | 10/2012 | Young | |
| 2013/0231594 A1 | 9/2013 | Bennett | |
| 2016/0120693 A1 | 5/2016 | Guillon et al. | |

FOREIGN PATENT DOCUMENTS

| | | |
|---|---|---|
| JP | H11352 A | 1/1999 |
| JP | 3116783 U | 11/2005 |
| JP | 2006517114 A | 7/2006 |
| JP | 2007143570 A | 6/2007 |
| JP | 3136038 U | 9/2007 |

OTHER PUBLICATIONS

International Bureau, International Preliminary Report on Patentability Chapter I for International Application No. PCT/US2010/043230, dated Jan. 31, 2012, pp. 1-10, Geneva, Switzerland.

International Bureau, Written Opinion of the International Search Authority for International Application No. PCT/US2010/043230, dated Jan. 26, 2012, pp. 1-9, Geneva, Switzerland.

International Bureau, Informal Comments by Applicant on WO-ISA for International Application No. PCT/US2010/043230, Jan. 26, 2012, pp. 1-21, Geneva, Switzerland.

\* cited by examiner

SELF-HEATED CONSUMER SPA PRODUCTS AND APPLICATIONS THEREOF

CROSS-REFERENCE TO RELATED APPLICATIONS

This application claims priority to U.S. Provisional Patent Application No. 61/228,590 entitled "Exothermic Therapeutic Massage Implements" and filed Jul. 26, 2009, U.S. Provisional Patent Application No. 61/228,593 entitled "Exothermically Heated Body Strips" and filed Jul. 26, 2009, U.S. Provisional Patent Application No. 61/228,595 entitled "Self-Heating Hair Treatment Strips and Bonnet" and filed Jul. 26, 2009 and also to U.S. Provisional Patent Application No. 61/228,596 entitled "Exothermically Heated Mitts and Booties" and filed Jul. 26, 2009. The contents of all of these United States Provisional Patent Applications are incorporated herein by reference in their entirety as if set forth verbatim.

FIELD

The following description relates generally to self-heated consumer spa products heated by means of a prolonged exothermic chemical reaction for various therapeutic and/or spa applications for applying heat to portions of a person's body.

BACKGROUND

For many years, the only manner in which personal skincare items in the spa market could be warmed or heated was by utilizing an external heat source. Typically, this source was a pot of boiling or hot water, an electric heating apparatus or other basic heating sources. In either case, while the warmth was certainly available for use, the risk of having that heating apparatus in the proximity of spa guests was significant. For instance, a spa guest could easily be scalded by hot water, and the danger of using electrical appliances in spa-type environments is widely known.

Moreover, the spa or salon and beauty industries have for many years made widespread use of coloring agents and hair treatments that require the application of heat to the treated area. Typically, a product that is heat reactive is applied to specified portions of the hair or scalp and heat is applied individually or en masse. For example, for highlighting hair using heat sensitive chemicals, the chemicals (some time pre-heated) are applied to hair segments (usually isolated from other hair segments by foil) and wrapping the treated hair with the foil and applying a hot air blow dryer to the hair for a prolonged period, or placing the person's head under a hot air hair dryer to activate the chemicals. Also, for revitalizing or straightening hair, some of the applied chemicals or oils are known to be more effective when heat is applied. For example, keratin proteins and amino acids require heat to dissolve, bond and strengthen hair.

Readily evident is the fact that the application of heat can be time consuming and often, the customer must wait for the various spa products and chemicals when they are pre-heated. Of course, the products can be heated to too hot a temperature, which lead to high discomfort for the treated person or in some cases, even burns. Therefore, the application of heat in a controlled manner is of important concern.

Many other uses require the generation of heat for application to portions of a person's body. For example, temperature elevation and maintenance for clothing and/or wearable articles is an ongoing issue for survival gear as well as for athletes, for spa and beauty, and medical personnel, to name a few. Traditional attempts to heat a person's body have included insulation wraps, thermal reservoirs, electrical resistance heating, chemically generated heat, dipping in hot water, and so forth. However, the heat generated can be very unstable and dangerous in some cases. Also, the duration of the heat is very limited resulting in the user having to "reapply" a new heated article (including the added time and effort to remove the old article and prepare the new article for placement). As can be seen, this can be a significant inconvenience and sometimes can result in a life-threatening oversight.

Moreover, most of this gear is directed, more or less, to a multiple use implementation, rather than something that can be of single use or limited use. Therefore, their weight is a substantial concern. The lack of popularity or widespread use of these products is a testimony to their inability to provide an adequately portable, cost-effective, lightweight, flexible, safe heating mechanism for warming for a prolonged period, a person or a part of a person's body.

Another common spa treatment is a popular therapeutic massage technique involving heating natural stones or ceramic implements and using them to massage different parts of the body of the massage recipient. Typically, the massage implements are heated with an external heat source such as a container of hot water or an electric heater. However, this approach has several drawbacks. First, the massage therapist must take care to not overheat the implements and burn the massage recipient, but at the same time ensure that the implements are hot enough to achieve their therapeutic purpose. Second, the implements begin cooling the moment they are removed from the external heat source. Even if the implements are at the desired temperature when they are first used, the implements constantly cool down until they must be returned to the external heat source. Thus, much of the time and effort of the massage therapist is occupied by shuttling implements between the heat source and the massage recipient, rather than being completely focused on performing the massage.

Methods of generating heat by using a non-apparatus driven heat source have been described in the following disclosure, along with various applications for self-heated consumer products. All of the products described utilize a heat producing reaction in various therapeutic and/or spa treatments to portions of a human body wherein the temperature must be maintained at a safe and comfortable rate, and the apparatus utilized for applying treatments at an elevated temperature must be specially designed to administer heat at a safe temperature for prolonged periods of time.

Accordingly, there is a need in the field to provide for various self-contained heating apparatuses for use in generating a prolonged heat-producing reaction to apply heat to portions of a human body that is both safe against skin and easy to use.

SUMMARY

The following simplified summary is provided in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the disclosed embodiments, an exothermically heated apparatus comprises an outer layer forming an open-ended enclosure capable of receiving a hand or foot; a heating layer interior to the enclosure, and an inner layer. The heating layer includes a first outer fabric layer, an exothermic layer activatable when contacted with an activating solution and a second outer fabric layer. In addition, the inner layer may also include at least one topical treatment composition.

In an alternative embodiment, the topical treatment composition includes at least one wax and at least one therapeutic composition, wherein the wax is solid at body temperature and becomes liquid when the exothermic compositions is activated thereby mixing with and facilitation distribution of the therapeutic composition.

In another embodiment of the disclosure, a self-heating, multi-layered, disposable fabricated sheet is provided, comprising: a flexible first layer; a flexible, water permeable second layer bonded at least to a perimeter of the first layer to form a pocket between the first layer and the second layer; and exothermic reactant disposed throughout the pocket, the exothermic reactant being activated by contact with an activator solution, generating non-scalding heat with non-toxic byproducts, wherein the permeable second layer operates via absorption to permit the liquid activator to be introduced to the exothermic material. The fabricated sheets of the present invention can be configured in any convenient shape, such as sheets, patches, and wearable "sleeves."

In a further embodiment, a self-heating, disposable hair treatment appliance is provided, comprising: a movably stiff, impermeable first layer capable of being positioned about a segment of hair and substantially retaining its position; a flexible, water permeable second layer bonded at least to a perimeter of the first layer to form a pocket between the first layer and the second layer, wherein a portion of the second layer section extends substantially beyond the perimeter of the first layer, exposing the second layer portion on a first layer side; and exothermic reactant disposed throughout the pocket, the exothermic reactant being activated by contact with a non-toxic solution, generating non-scalding heat with non-toxic byproducts, wherein the permeable second layer operates via absorption to permit the non-toxic solution to be introduced to the exothermic reactant.

In another aspect of the disclosure, a self-heating, disposable bonnet is provided, comprising: a flexible, first layer sized to fit about a person's scalp; a flexible, water permeable second layer bonded at least to a perimeter of the first layer to form a plurality of pockets between the first layer and the second layer; and exothermic reactant disposed throughout the plurality of pockets, the exothermic reactant being activated by contact with a non-toxic activator, generating non-scalding heat with non-toxic byproducts, wherein the permeable second layer operates via absorption to permit the non-toxic activator to be introduced to the exothermic reactant.

In various other embodiments, an exothermic massage implement, such as an artificial stone, shell or natural bamboo stick, includes a heat conducting vessel having an inner chamber surrounded by a wall with an inner surface and an outer surface. A reactant is inside the inner chamber of the vessel. Combining the reactant with an activator causes an exothermic reaction that heats the wall and maintains the wall at a substantially constant elevated temperature for a duration of time.

There may also be at least one aperture in the wall, which may be covered by a cap engaged with the aperture, wherein the cap sequesters the combined reactant and activator inside the inner chamber of the massage implement, and wherein the cap further comprises a vent hole that allows gas flow out of the inner chamber of the massage implement.

The vessel containing the mixture in its inner chamber may be ceramic. The outer surface of the wall may have portions with an abrasive texture and portions with a smooth texture.

The powder mixture inside the inner chamber of the vessel may also include sodium chloride particles, and the activator may be water. The powder mixture may be contained within a water-permeable pouch inside the inner chamber. The vessel may be ceramic. The vessel may also be in the shape of a rolling pin with a hollow core. Alternatively, or additionally, other shapes which may have an ergonomic attribute or function, or aesthetic design may be used.

In another embodiment, an exothermic massage implement includes a heat conducting artificial stone having an inner chamber surrounded by a wall with an inner surface and an outer surface. A powder mixture is contained inside the inner chamber of the artificial stone. This powder mixture includes at least reactant particles. When the powder mixture is combined with an activator, an exothermic gel is created. This exothermic gel heats the artificial stone wall and maintains the artificial stone wall at a substantially constant elevated temperature for a duration of time.

Additionally, the outer surface of the wall may have portions with different radii of curvature and different textures, such that the user can use the same vessel for a variety of different modes of treatment.

In a further alternative embodiment, an exothermic massage implement may further comprise a stopper having a vent hole and a cap affixed to an end of the heat conducting vessel. In various embodiments, the exothermic massage implement may be constructed from bamboo.

In another embodiment, reactant may be affixed to a sheet and rolled into a tubular shape prior to being placed in the inner chamber of a heat conducting vessel. Additionally, the tubular sheet may be sealed in a water soluble paper wrapper prior to use. Further, the tubular sheet sealed in the water soluble paper wrapper may be further sealed in a water soluble plastic film wrapper.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

DETAILED DESCRIPTION

Figure 1:
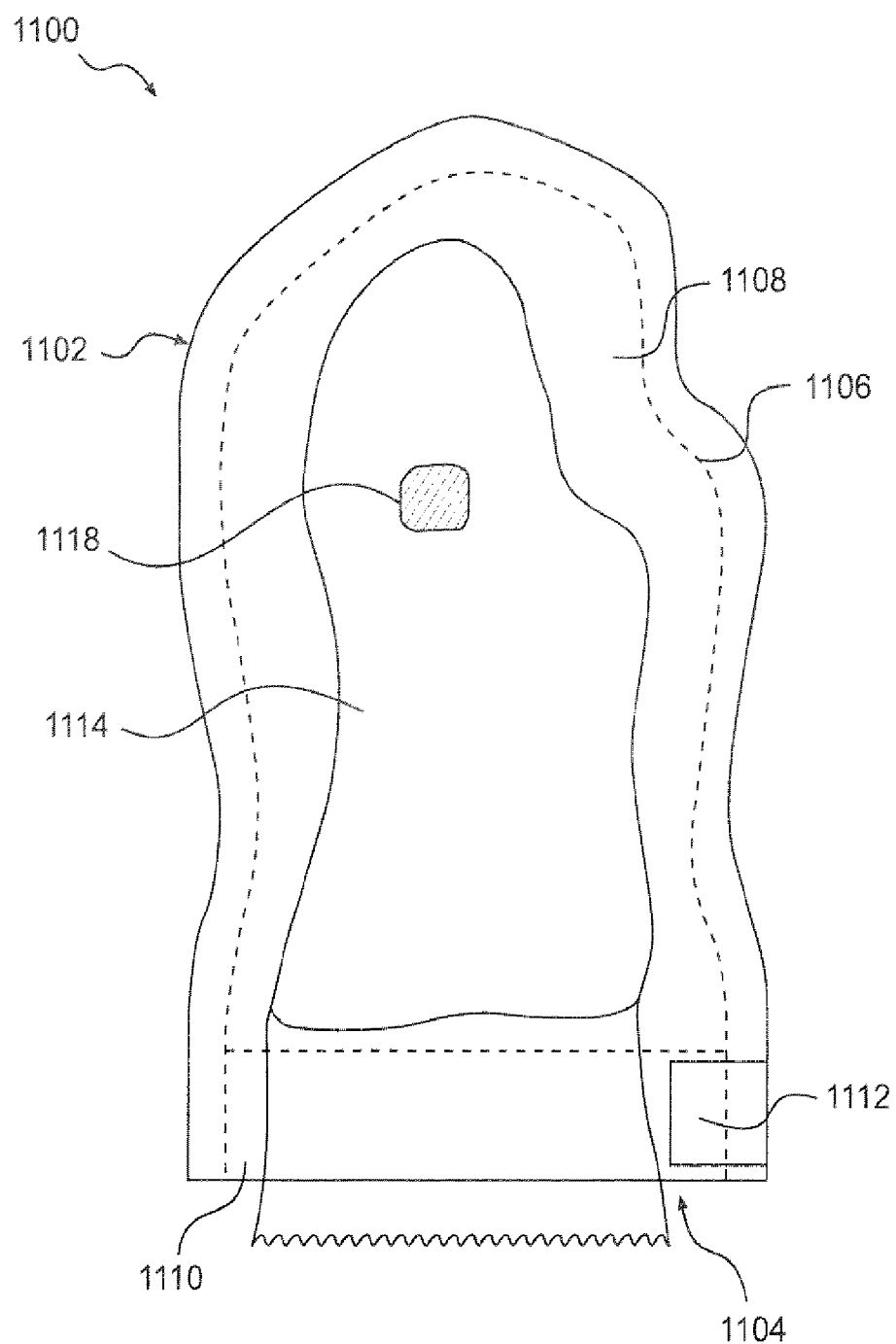
FIG. 1 illustrates a top plan view of an embodiment of an exothermically heated mitt.

The following description relates generally to self-heated consumer spa products heated by means of a prolonged exothermic chemical reaction for various therapeutic and/or spa applications for applying heat to portions of a person's body.

Additionally, the disclosure further relates generally to an exothermically heated apparatus for applying a topical treatment to a local area on a person. While various embodiments are shown in the drawings, it should be understood, however, that they are to be considered an exemplification of the principles of the invention and are not intended to limit the spirit and scope of the subject matter described herein and/or claims of the embodiments illustrated.

In various embodiments disclosed herein, the mechanism for heat is an exothermic composition that generates heat upon activation by an activator. The exothermic composition is provided around or inside strips, patches, or a sleeve designed for the exothermic composition. Examples of exothermic compositions that can be used may come from the combination of water with strong acids, combining alkalis and acids, polymerization, thermite reactions, aluminum-based, magnesium-iron-based reactions, anhydride reactions, and so forth. One particularly suitable, non-toxic exothermic compound is Lava Gel® (manufactured by Forever Young International, Inc., Escondido, Calif., USA) which is known to exhibit a very controlled, regulated temperature for an extended period of time, with simply the addition of water or an electrolyte solution, such as saline water (as the activator). However, other exothermic compositions may be used, accordingly to design preference, including compositions that require activation or moderation by more than one activator or other compounds or elements.

By use of a non-electrical or non-fossil fuel heating source, the embodiments herein can be considered as self-contained units, portable, and also disposable with minimal to no environmental consequence. With a regulated, controlled exothermic reaction, overheating can be avoided, as well as burns that occur from such overheating. That is, by having heat readily generated and easily maintained, heating for purposes, such as therapeutic, emergency, healing, frost bite recover, and so forth, can be more readily implemented. The advantages of such a self-contained product, as described herein, can be well appreciated by active sportsmen, medical teams, home users, outdoorsman, etc., to list a few of the many possible beneficiaries. In principle, a lightweight, flexible, safe heating mechanism for warming for a prolonged period, a person or a part of a person's body is now described.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

Further, unless defined otherwise, all terms used herein have the same meaning as are commonly understood by one of skill in the art to which this invention belongs. All patents, patent applications and publications referred to throughout the disclosure herein are incorporated by reference in their entirety.

Mitts and Booties

Referring now in detail to the drawings, FIG. 1 illustrates an exothermically heated apparatus 1100. The exothermically heated apparatus 1100 includes an outer layer 1102 which forms an open-ended enclosure 1104. In the exemplary embodiment illustrated in FIG. 1, the outer layer 1102 may be prepared by providing a front and a back covering with a seal 1106 about its perimeter. Alternatively, in another embodiment, the outer layer 1102 may be of a single and unitary construction. In one embodiment of the invention, the outer layer 1102 may be constructed with a polyethylene (PE) film. However, any water-impermeable material known to one skilled in the art would be suitable for construction of the outer layer 1102. As shown in FIG. 1, the open-ended enclosure 1104 is shaped in the form of a mitt or glove capable of receiving a hand. One of skill in the art can appreciate that in alternative embodiments of the present invention, the open-ended enclosure 1104 may be formed into varying shapes, such as in the form of a bootie capable of receiving a foot. FIG. 1 further illustrates a tab 1112 for securing an open-ended cuff 1110 around a person's wrist or ankle. The tab 1112 may be an adhesive strip, button or any other suitable means of securing the open-ended cuff 1110.

Figure 2:
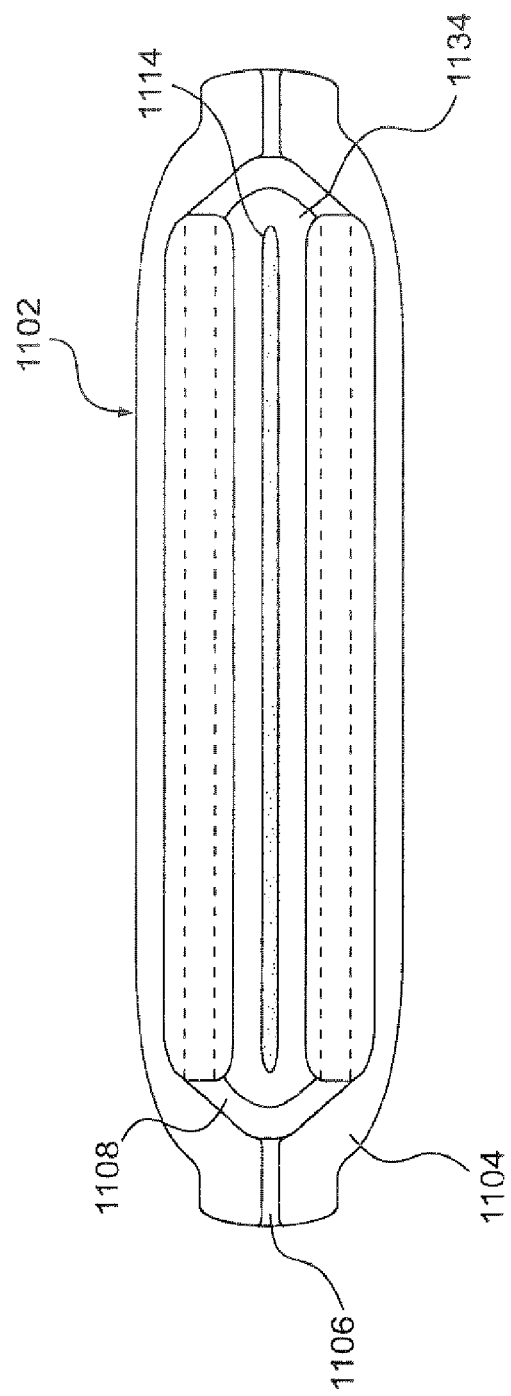
FIG. 2 illustrates a cross-sectional drawing of an exothermically heated apparatus.

A heating layer 1108 is secured within the exothermically heated apparatus 1100, and may be accessible through the open-ended cuff 1110. Referring now to FIG. 2, a heating layer 1108 is provided for placement interior to the open-ended enclosure 1104 and may be prepared by providing two symmetrical layers of heating panels connected by a seal 1106. Alternatively, the heating layer 1108 may be of a single and unitary construction. A gap 1134, or space, is provided between the heating layer 1108 and a liner 1114, which will be discussed elsewhere in further detail.

Figure 3:
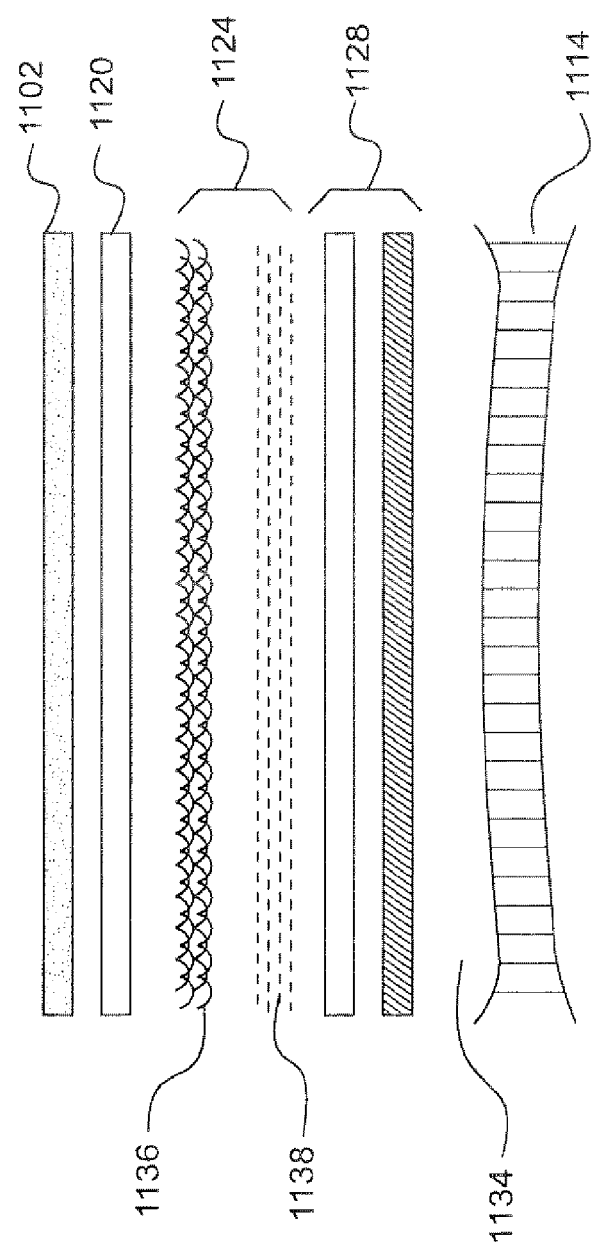
FIG. 3 illustrates an enlarged view of the cross-sectional drawing of FIG. 2.

Referring now to FIG. 3, which illustrates an enlarged perspective of a portion of the exothermically heated apparatus 1100, the outer layer 1102 is provided on the outside of the exothermically heated apparatus 1100. A heating layer 1108 is placed interior to the open-ended enclosure 1104 within the outer layer 1102. The heating layer 1108 is comprised of a first outer fabric layer 1120, an exothermic layer 1124 and a second outer fabric layer 1128. In an exemplary embodiment, the first outer fabric layer 1120 may be composed of tissue paper or a similar material.

The exothermic layer 1124 may be comprised of a polymeric layer 1136, such as a nonwoven fabric. In an exemplary embodiment, the polymeric layer 1136 is a nonwoven coarse yet flexible polymeric fabric, such as those used in medical underpad applications. The exothermic layer 1124 is further comprised of an exothermic composition 1138, which may be provided impregnated onto or within the polymeric layer 1136. The exothermic composition 1138 may include minerals which exhibit exothermic reactions, such as those using reduction reactions of calcium (e.g. quick-lime) and magnesium-iron alloys.

Exothermic reactions generated by these exemplary exothermic compositions are typically initiated using water, or an electrolyte solution such as salt-water. In an exemplary embodiment, an exothermic reaction may be activated by contacting the exothermic layer 1124 with an activating solution such as water or an electrolyte solution. Activation of the exothermic reaction may therefore be achieved by pouring the activating solution into the gap 1134 provided between the heating layer 1108 and the liner 1114.

A second outer fabric layer 1128 is provided beneath the exothermic layer 1124 and may be prepared with one or more fabric materials. For example, as shown in FIG. 3, the second outer fabric layer 1128 may be composed of a layer of tissue paper and an additional layer of nonwoven fabric such as polypropylene spun lace.

As discussed previously, FIGS. 1 and 2 also illustrate a liner 1114 which is placed interior to the heating layer 1108. In an exemplary embodiment, a gap 1134 separates the heating layer 1108 from the liner 1114. The liner 1114 is composed of a water-impermeable material to protect a hand or foot from direct exposure to the heating layer 1108. Non-limiting examples of water-impermeable materials include natural and synthetic rubbers, polyvinyl chloride, ethylene-vinyl acetate copolymers, polyurethanes, acrylic ester polymers, polyamides and the like.

In an exemplary embodiment, the liner 1114 is provided with a topical treatment composition 1118. The treatment composition 1118 may be comprised of at least one wax, oil, skin treatment compositions, or other types of therapeutic compositions that, once they penetrate the skin, have a systemic therapeutic effect. In one embodiment, the topical treatment composition 1118 may constitute a wax, an oil carrier and a skin treatment composition. However, it is to be understood that the topical treatment composition 1118 may be comprised solely of a wax, oil, or skin treatment composition compound or any combination thereof.

Examples of various types of wax suitable for use in the treatment composition 1118 include paraffin, beeswax and Soyaffin® serum (manufactured by Forever Young International, Inc., Escondido, Calif., USA). Furthermore, examples of oil include essential oils and absolutes. An oil carrier may also be mixed in with the oil if necessary depending on the oil, as is common in the spa and therapeutic business. It is to be appreciated that a variety of waxes and oils may be suitable for use in the treatment composition 1118.

Additionally, a number of skin treatment compositions may be provided in the topical treatment composition 1118. In exemplary embodiments, any cosmetic or therapeutic compound, or combination thereof, which may be referred to as a "cosmeceutical," may be suitable for use in the topical treatment composition 1118 in the liner 1114. Additionally, in alternative embodiments, heat-enhancible topically administered compositions are also contemplated. Examples of heat-enhancible compositions include heat-activated skin care products such as Venuceane™ (manufactured by Sederma, Le Perray-en Yvelines Cedex, France), bio-active enzymes such as those derived from *Thermus thermophilus* and anti-aging peptides such as Palmitoyl-pentapeptide-4. Other heat-activated products include therapeutic compounds for pain relief such as camphor, menthol, capsaicin and witch hazel. Herbal products such as natural extracts like green tea, grapefruit seeds and *yucca* root may also be suitable for use as a topical as well.

One of ordinary skill in the art will understand that a number of topically administered ingredients can be combined with a wax and oil in the topical treatment composition 1118 provided in the liner 1114 as described for applying therapeutic or cosmetic treatment. In an exemplary embodiment, the wax, oil and topical are combined together in the treatment composition 1118 as shown in FIG. 1. In an alternative embodiment, each component of the treatment composition 1118 may be provided at different locations in the liner 1114. For example, a solid wax and oil mixture may be provided in the liner 1114 at a separate location than the topical such that when the exothermic reaction is activated, the wax and oil mixture liquefies and combines with the topical.

Figure 4:
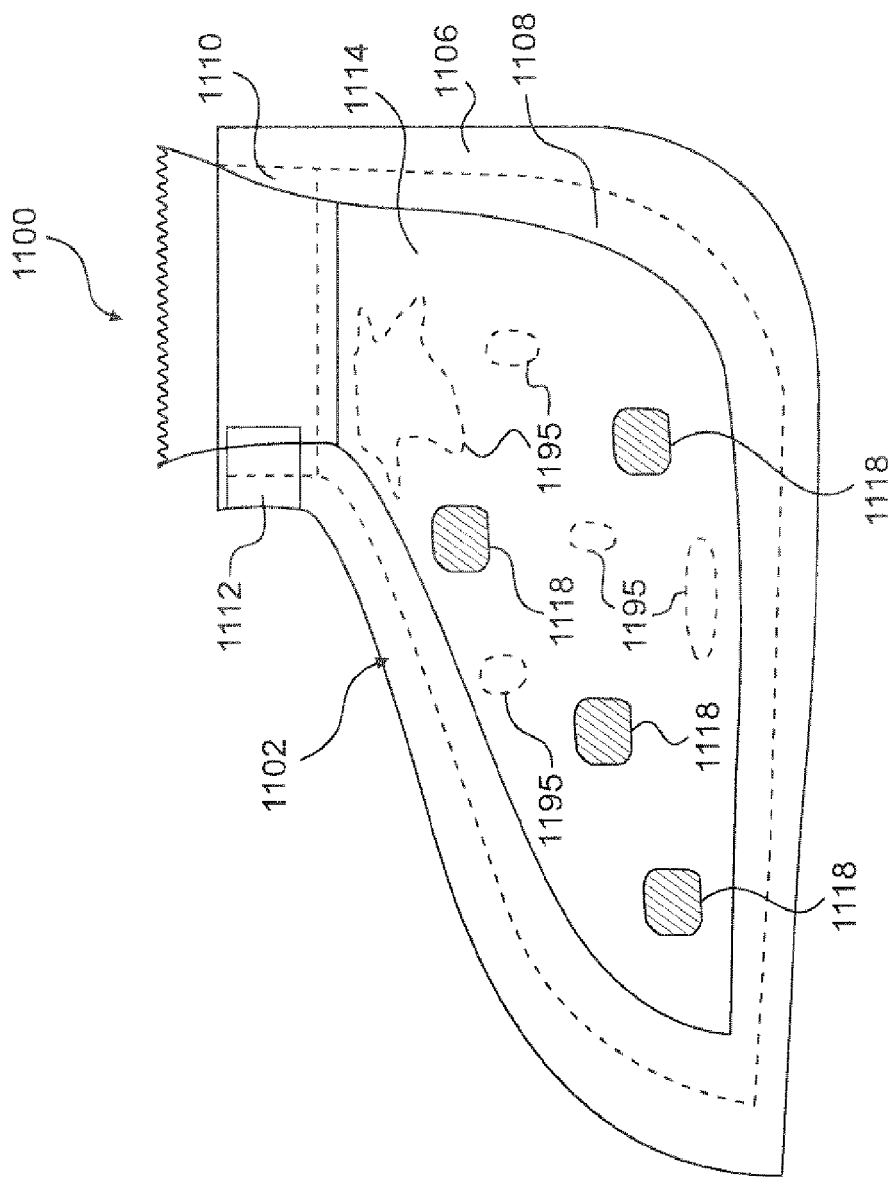
FIG. 4 illustrates a top plan view of an embodiment of an exothermically heated bootie.

FIG. 4 illustrates an alternative embodiment as described in FIG. 1, wherein the exothermically heated apparatus 1100 is formed in the shape of a bootie capable of receiving a human foot. Additionally, in the embodiment, the treatment composition 1118 is provided in multiple locations within the liner 1114. As discussed previously, the treatment composition 1118 may comprise a wax, oil and topical combination or any combination of the components, such as a wax and oil mixture. Further, the treatment composition 1118 may comprise different combinations of products at separate locations in the liner 1114. For example, a solid wax and oil mixture may be provided in the liner 1114 at the upper surface of the exothermically heated apparatus 1100 shaped in the form of a bootie, while a heat-activated topical such as Venuceane™ may be provided in the liner 1114 at the lower surface of the bootie.

Any one or more of the wax, oil, treatments (compositions), ointments, topicals, and so forth may be distributed about the liner 1114, as shown for example, as element(s) 1195. Additionally, the solid wax or oil mixture may be independent/different from the element(s) 1195. That is, different compositions or chemicals or substances can be displaced within the line 1114, having different heat responsive characteristics, as well as specified locations. For example, inside palm ointments, etc., may be of a different composition that outside palm ointments, etc. Thus, variations to the type of materials put into the liner 1114 and their location may be made without departing from the spirit and scope of this disclosure.

Body Strips

In various other exemplary embodiments, a multi-layered disposable material is utilized, (i.e., a "fabricated sheet"), housing an outer layer and an inner layer, with an intermediate layer of exothermic reactant. Activation of the exothermic reactant is achieved by applying or soaking the exemplary embodiment(s) in an activating solution, such as an electrolyte solution or water, which triggers the exothermic reaction to generate the desired heat.

In various exemplary embodiments, the design of the multi-layered disposable material is such that it can be manufactured from plastic, water proof paper, woven fabrics, foil, natural fibers, and so forth. One layer of the multi-layered disposable material may be of a semi-permeable or even permeable material that permits entry of the activating solution into the exothermic material that is embedded or sandwiched therein. Certain portions of the semi/permeable layer may be configured with adhesive strips or gripping sections for ease of manipulation and fastening.

The other layer, on the opposite side of the multi-layered disposable material, may be of an impermeable or semi-permeable material that restricts the entry or exit of water or the activating solution. The impermeable or semi-permeable layer can operate as a barrier to the water or activating solution, thus isolating the user's skin or body part from contact with moisture retained in the interior of the exemplary embodiment. Also, certain portions of the impermeable/semi-permeable side may be configured with adhesive strips or gripping sections for ease of manipulation and fastening.

Figure 5:
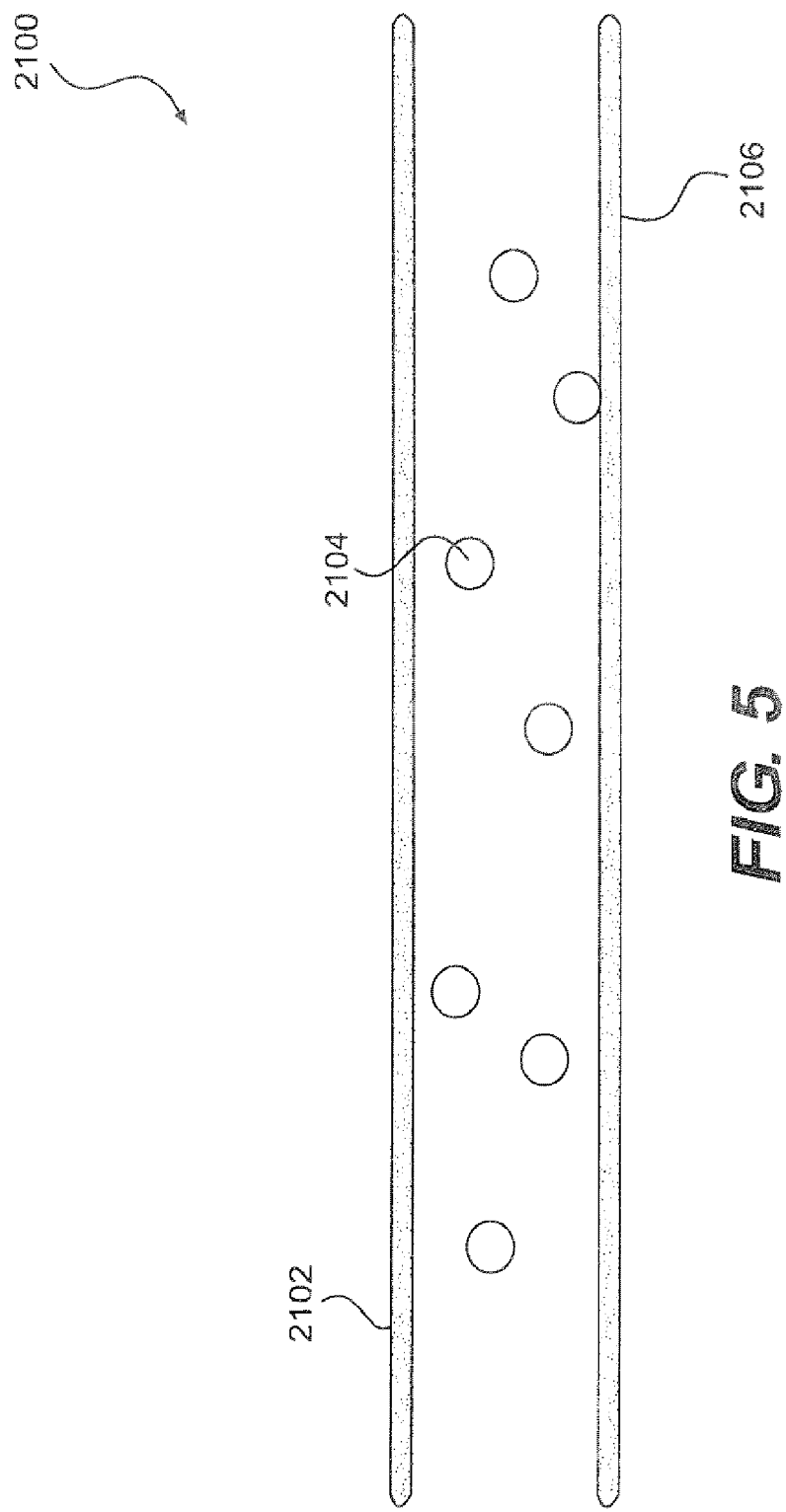
FIG. 5 is a perspective view of an exemplary self-heating fabricated sheet.

Referring in detail to the drawings, FIG. 5 illustrates an exothermically self-heating multi-layered fabricated sheet 2100. The exothermically self-heating multi-layered fabricated sheet 2100 comprises an outer layer 2102, exothermic reactant 2104, and inner layer 2106. The outer layer 2102 may be any water-permeable material known to one skilled in the art. The exothermic reactant 2104 may be any material that can be activated by the introduction of an activating solution, such as water or an electrolyte solution (e.g., saline solution), that also exhibits a controlled release of heat without burning the wearer, and is capable of maintaining its heat for a prolonged period of time. As mentioned above, Lava Gel® has been found to be a suitable exothermic reactant, having the above characteristics and also being non-toxic. Inner layer 2106 can be an impermeable material so that any liquid introduced into the outer layer 2102 does not leak through the inner layer 2106.

To activate the self-heating multi-layered fabricated sheet 2100, the user may simply dip the sheet (with the permeable side exposed) into the activating solution (if using Lava Gel®, then water can be the activating solution) and letting the activating solution soak into the exothermic reactant that is bounded by the inner and outer layers. Some degree of shaking may be needed, to better distribute the activating solution. After a couple of minutes, the self-heating multi-layered fabricated sheet 2100 will rise to its desired/designed temperature and maintain itself at that temperature for an extended period of time. Using Lava Gel®, extended heat times of over an hour or more can be achieved.

It is known that Lava Gel® will "fluff" up or expand within the inner and outer layers as it activates, so it is possible to wrap the multi-layered fabricated sheet 2100 around a person or article and allow the "fluffing" to provide pressure to the applied areas. Also, because of the fluffing characteristic, cavities or bends or depressions in the applied areas can be filled in by the fluffing, thereby resulting in the application of heat to those contacted filled in areas that would most likely not be contacted by other non-fluffing exothermics.

In some embodiments, it may be desirable to have both inner layer 2106 and outer layer 2102 as impermeable layers, using a port or channel in either layer for introducing the exothermic activating solution. In these embodiments, no activating solution need be exposed to the elements (or drip out) after being applied to the self-heating multi-layered fabricated sheet 2100, as well as the fact that with a permeable membrane or layer, heat can escape through the membrane, which could reduce its heating longevity.

As should be appreciated from the above description, variations and modifications to the layers and material described above may be made without departing from the spirit and scope of this disclosure. For example, the layers may be formed in strips (laterally alternating), whereby one strip or section of outer layer 2102 would be impermeable and another neighboring strip or section of outer layer 2102 would be permeable. Thus, different regions of the self-heating multi-layered fabricated sheet 2100 would be heated. An example would be the use of a wrap wherein only one section of the wrap would be self-heating, for localized heating (e.g., knee, calf, shoulder, etc.). In other embodiments, it is envisioned that the permeable layer may have an impermeable tear-off covering, and by tearing off appropriate impermeable tear-off cover(s), selected portions or sections of the self-heating multi-layered fabricated sheet 2100 would be heated.

From the above, it is apparent that additional layers of fabric or material may be utilized to enhance the capabilities and uses for the self-heating multi-layered fabricated sheet 2100. In some instances, exothermic material 2104 may be layered between several fabric layers, or embedded in an intermediate layer, according to design purposes. Thus, having understood the disclosure provided herein, variations to the self-heating multi-layered fabricated sheet 2100, in layering, construction, type, etc., for example, are within the purview of one of ordinary skill in the art.

Figure 6A:
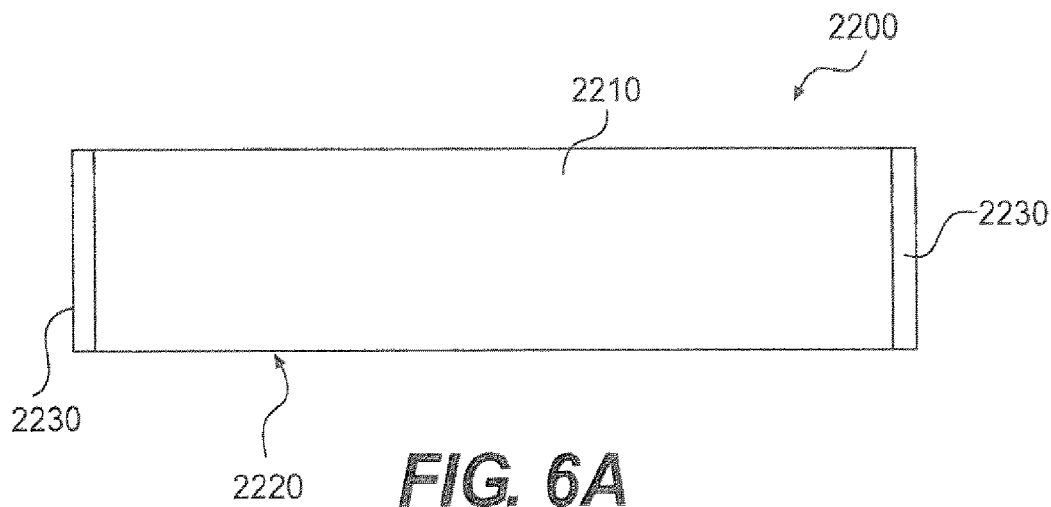
FIG. 6A is a view of an exemplary strip of self-heating fabricated sheet.

FIG. 6A is a front view of an exemplary multi-layered strip 2200, containing front 2210, back 2220, and optional attachment strips 2230. Not shown, but disposed in between the front 2210 and back 2220 of the exemplary strip 2200 is exothermic material, such as, for example Lava Gel®. The front 2210 can be constructed from an impermeable material and the back 2220 can be comprised of a permeable or semi-permeable material that can absorb the activating solution (not shown) and also allow exhaust gases to exit when the exothermic material is activated. In this example, when using Lava Gel® as the exothermic material, the activating solution can be water or a saline solution.

Edges of exemplary strip 2200 can be bonded or sealed and the right and left sides of the exemplary multi-layered strip 2200 can be exposed back layer 2220, via the optional attachment strips 2230. Of course, the terms left, right, top, bottom, are relative terms and may be interchanged according to design preference. Sections of the exemplary multi-layered strip 2200 may contain an adhesive for fastening purposes.

In one mode of application, the user of the exemplary multi-layered strip 2200 may "pre-heat" the exemplary multi-layered strip 2200 by applying water/activating solution prior to application or, "post-heat" the exemplary multi-layered strip 2200 by applying water/activating solution after application.

Because the exemplary multi-layered strip 2200 is narrow, it can be wrapped around individual parts of the human body or around an article (for example, outdoor water faucet). It can be fastened by conventional means or by the optional attachment strips 2230. After the desired period of use, the exemplary multi-layered strip 2100, being of single/limited use, can be removed and discarded. Accordingly, sanitation concerns from re-using heating devices need not be a concern.

It should be appreciated that while the exemplary multi-layered strip 2200 is shown as having a rectangular form, other forms or shapes for the exemplary multi-layered strip 2200 may be contemplated. For example, an oval, circular, serpentine, and other various shapes, forms, designs, contours and so forth, may be devised according to design preference. Therefore, the strip-like shape shown can be modified in any reasonable manner desired, without departing from the spirit and scope of this disclosure.

Figure 6B:
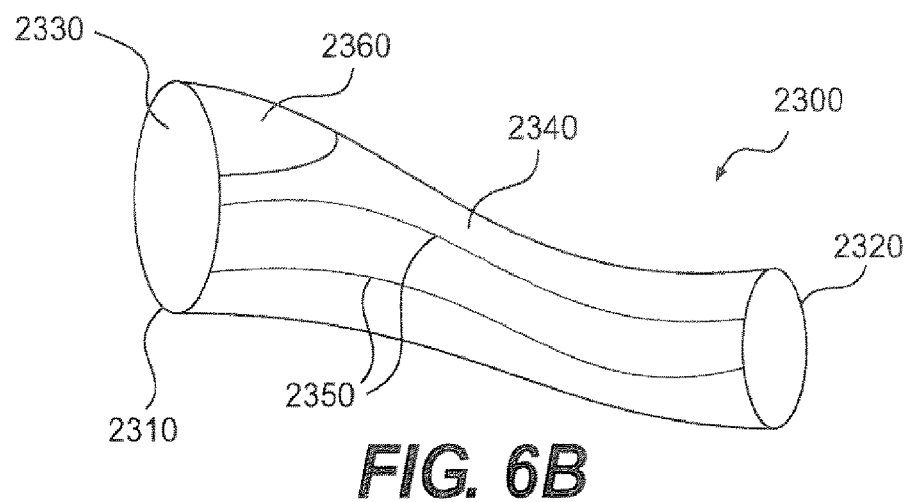
FIG. 6B is an illustration of an exemplary self-heating sleeve.

FIG. 6B is an exemplary embodiment of a sleeve 2300 formed from the exemplary multi-layered fabricated sheet 2100. The exemplary sleeve 2300 is configured with shoulder-side opening 2310, wrist-side opening 2320, inner layer 2330, outer layer 2340 and optional seams 2350 and optional protective area 2360. The inner layer 2330 and outer layer 2340 may be any combination of permeable/impermeable materials, as discussed above. Alternatively, in another embodiment, the sleeve 2300 formed from the exemplary multi-layered fabricated sheet 2100 may be configured to fit around a portion of a leg.

In one embodiment, it is contemplated that the inner layer 2330 is impermeable (thereby mitigating the wetting of the wearer's arm) and the outer layer 2340 is permeable, allowing an entry point for the activating solution and also an exit point for the exhaust gases from activation via the permeable outer layer 2340. Exemplary sleeve 2300 can be activated a priori or activated after application, in accordance with steps described above. The protective area 2360 is optionally provided to prevent any exhaust gases from approaching the wearer's face, if so desired. Optional seams 2350 are presented as means for "channeling" the activating solution and/or exothermic material. In some embodiments, an aperture (not shown) can be provided for enabling a focal point for activation solution entry. As can be imagined, with a permeable layer and impermeable layer, so configured, the exemplary sleeve provides the wearer the option of having a "dry" heat (impermeable layer side) or "wet" heat (permeable layer side), by simply inverting the exemplary sleeve 2300.

Figure 6C:
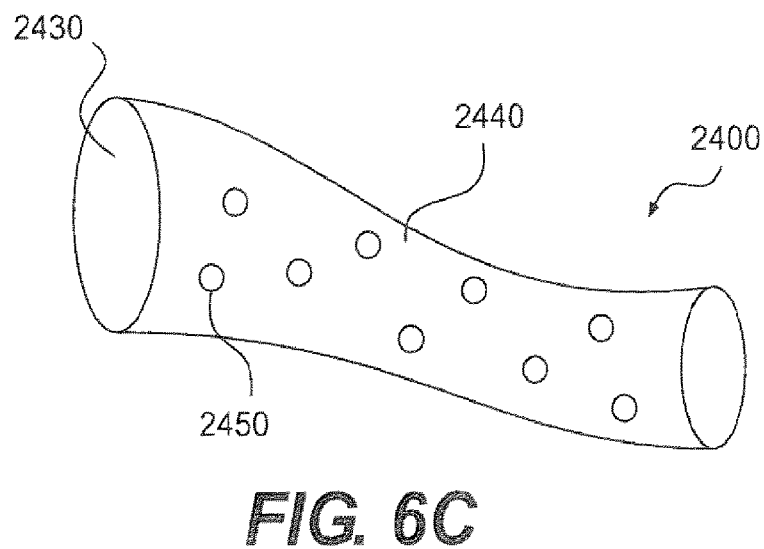
FIG. 6C is an illustration of another exemplary self-heating sleeve.

FIG. 6C an exemplary embodiment of a sleeve 2400 formed from the exemplary multi-layered fabricated sheet 2100, wherein venting ports 2450 are distributed along the outer layer 2440. The embodiment of FIG. 6C allows both the inner layer 2430 and outer layer 2440 to be of impermeable material. Of course, in some instances, outer layer 2440 may be designed with a semi-permeable material, if so desired.

It should be understood that the embodiments illustrated herein are demonstrative of other possible embodiments. For example, the embodiments of FIGS. 6B-C may be altered to accommodate a leg or calf or other part of the body. Also, the embodiment of FIG. 6A may be used in combination with the embodiments of FIGS. 6B-C. As mentioned above, while these exothermic designs are generally described in the context of use upon a human, they may be used on non-humans (animals, for example), plants, objects, and other conceivable things/materials that would benefit from a stable, wrapable (or attachable), self-heating source, that is non-toxic and disposable.

Bonnet

In various other exemplary embodiments, a multi-layered disposable material is utilized, (i.e., a "fabricated sheet"), housing an outer layer and an inner layer, with an intermediate layer of exothermic reactant. Activation of the exothermic reactant is achieved by applying or soaking the exemplary embodiment(s) in an activating solution, such as an electrolyte solution or water, which triggers the exothermic reaction to generate the desired heat.

In various exemplary embodiments, the design of the multi-layered disposable material is such that it can be manufactured from plastic, water proof paper, woven fabrics, foil, natural fibers, and so forth. One layer of the multi-layered disposable material may be of a semi-permeable or even permeable material that permits entry of the activating solution into the exothermic reactant that is embedded or sandwiched therein. Certain portions of the semi/permeable layer may be configured with adhesive strips or gripping sections for ease of manipulation and fastening.

Various embodiments disclosed below are suitable in conjunction with the application of various heat-activated chemical compositions. For example, keratin proteins and other amino acids are known to be more effective after being activated by heat.

Figure 7A:
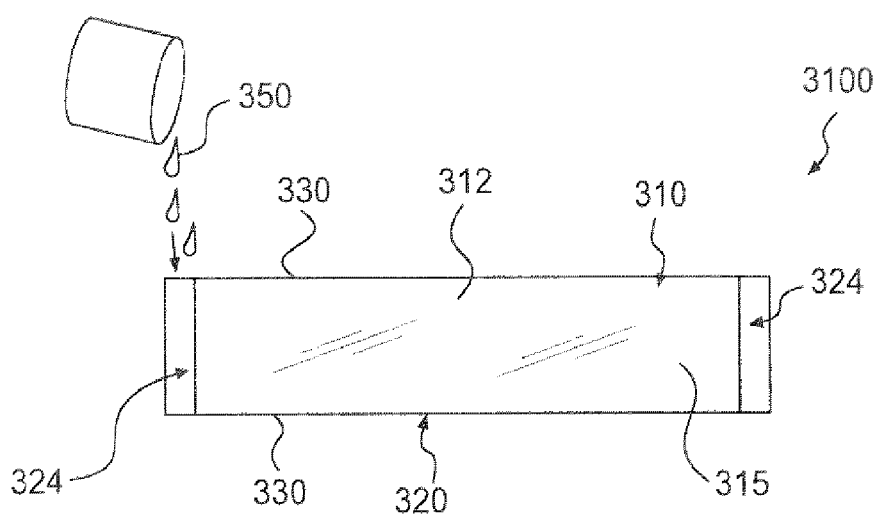
FIG. 7A is a perspective view of an exemplary disposable hair strip.

Referring now in detail to the drawings, FIG. 7A is a front view of an exemplary disposable hair strip 3100, containing front 310, back 320, and foil 312. Not shown, but disposed in between the front 310 and back 320 of the exemplary strip 3100 is exothermic reactant, such as, for example, Lava Gel®. The front 310 is surfaced with the foil 312 while the back 320 is comprised of a permeable or semi-permeable material that can absorb the activating solution 350 and also allow exhaust gases (for example, non-toxic steam or vapors) to exit when the exothermic reactant is activated. In this example, when using Lava Gel® as the exothermic reactant, the activating solution 350 can be water or a saline solution.

Edges of exemplary strip 3100 can be bonded or sealed 330 to hold the exothermic reactant, and the right and left sides of the exemplary strip 3100 can be exposed, having a non-foil extension 324. That is, back 320 having the permeable or semi-permeable material may be exposed via the removal of a peelable or otherwise removal seal (not shown) along the non-foil extension 324 sections, to allow "wicking" of activating solution 350 when applied thereto. Also, exposed non-foil extension 324 can also operate as a gripping section, if the heat sensitive chemical is already applied to front 310 foil side. Further, sections of the exemplary strip 3100 may contain an adhesive for fastening purposes. Or alternately, the foil 312 structure may be crimped and folded around the hair (segments). In some embodiments, it may be desirable to not have the non-foil extension 324. That is, the entire face of the back 320 may be covered with foil 312, if so desired.

It should be understood that the term foil as used in the context of this description is a general term and, in some embodiments, a semi-rigid membrane, for example, may be used. In the hair industry, the ability to fold, crimp, attach, bend and so forth are some attributes desired by hair professionals. Therefore, while the various descriptions herein use the term foil, it is understood that other materials, whether metallic in nature or not, that provide some or all similar characteristics (as they pertain to the hair or scalp industry) may be used without departing from the spirit and scope of this disclosure.

In one mode of application, the user of the exemplary strip 3100 may "pre-heat" the exemplary strip 3100 by applying water/activating solution prior to application or, "post-heat" the exemplary strip 3100 by applying water/activating solution after application. The later approach may be more amenable to conventional treatment approaches, where the "heat" is applied after the foil element is fixed to the subject. The later approach can be achieved by adding the activating solution 350 to the non-foil extension 324 or via the unsealed back 320.

Figure 7B:
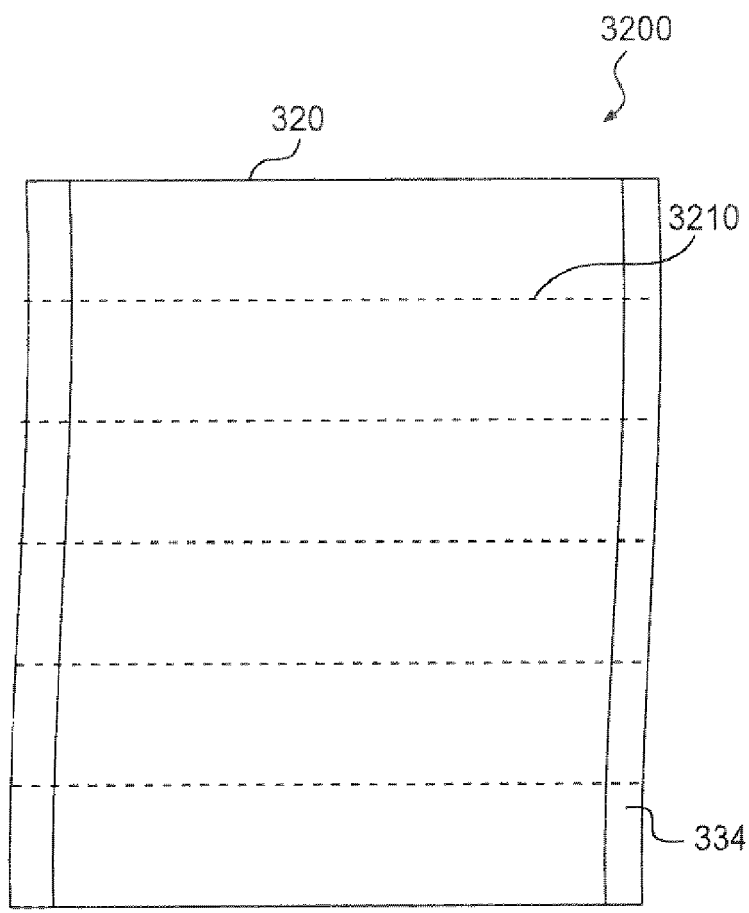
FIG. 7B is a top side view of an exemplary embodiment of a sheet of exemplary strips.

FIG. 7B is an exemplary embodiment of a sheet 3200 of exemplary strips 3100, having a "tear away" boundary between neighboring strips 3100. The exemplary sheet 3200 permits multiple strips 3100 to be fabricated in bulk and similarly shipped in bulk to customers. The lateral edges (non-foil extension 324) may be covered with a removable membrane (e.g., seal) or cover to prevent any moisture from prematurely entering the embedded exothermic reactant. Additionally, the back 320 may be covered with a seal, for similar reasons. The removable membrane or seal can be removed when the exemplary strip 3100 is readied for use.

As is well known, methods and means for generating tear away sheets or strips are common to the fabric and material industries, and therefore they are not further detailed herein.

It should be appreciated that while the exemplary strips 3100 are shown as having a rectangular form, other forms or shapes for the exemplary strips 3100 or sheet 3200 may be contemplated. For example, an oval, circular, serpentine, and other various shapes, forms, designs, contours and so forth, may be devised according to design preference. Therefore, the strip-like shape shown can be modified in any reasonable manner desired, without departing from the spirit and scope of this disclosure.

Figure 8:
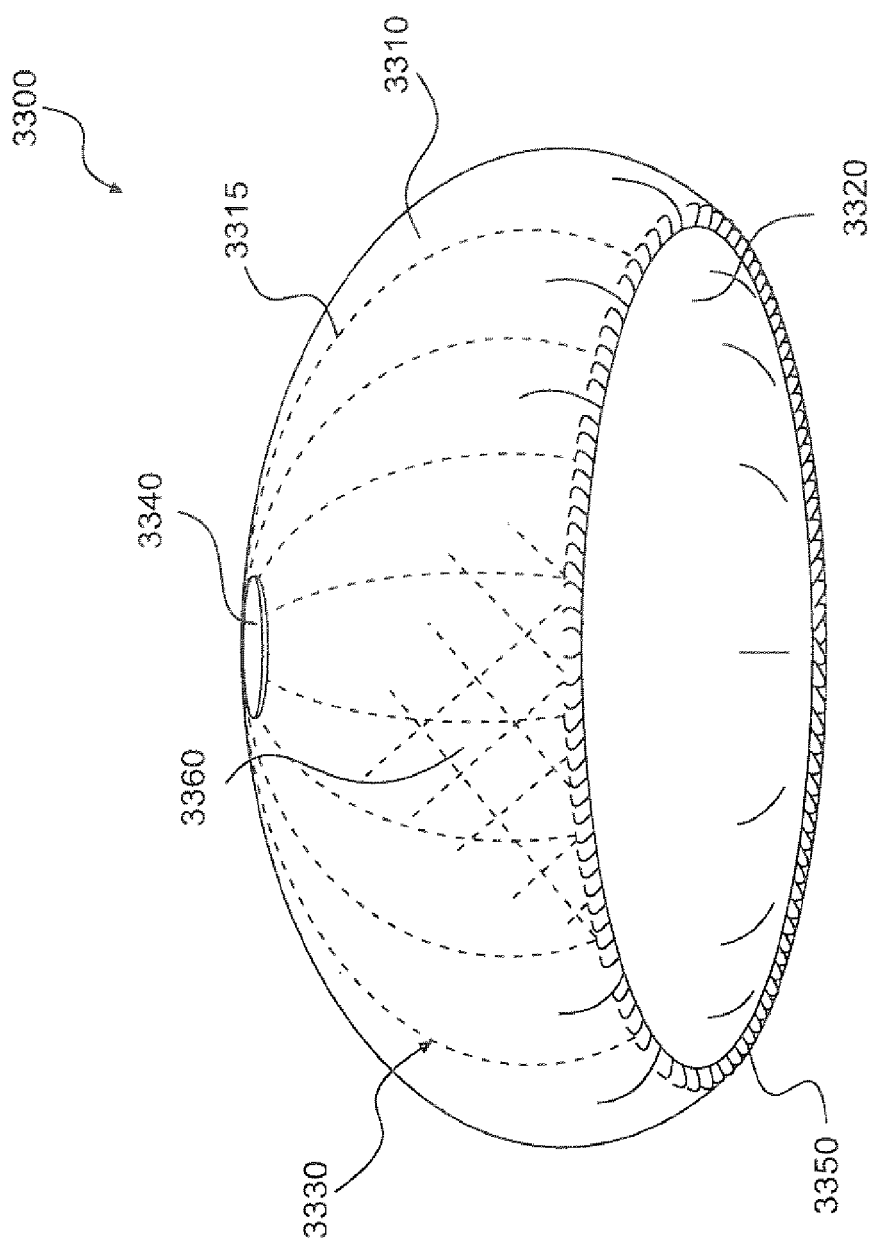
FIG. 8 is a perspective view of another exemplary bonnet.

One example of the exemplary strip 3100 being formed into a non-strip shape is shown in FIG. 8, where a bonnet or cap 3300 is formed to cover the head of a user. The exemplary bonnet 3300 can be used by placing exemplary strips 3100 into the bonnet sleeves, or alternatively, the exemplary bonnet 3300 can be pre-configured with the stable exothermic reactant to provide the desired heat and duration of heat. The efficacy of the bonnet 3300 is that, rather than using the exemplary strips 3100 to generate the needed heat, a heat generating bonnet 3300 can be worn to achieve the desired effect. With such a bonnet 3300, the user can now be mobile, walk around, do chores, etc., without having to sit under a hot air hair dryer. This can be a desirable attribute, as hot air hair dryers are known to be noisy, disrupting conversations, as well as being expensive and sometimes prone to failure.

As shown in FIG. 8, the exemplary bonnet 3300 comprises an outer layer 3310, inner layer 3320, chamber 3330 and (optionally) activation solution entrance aperture 3340. Depending on the desired use, outer layer 3310 may be of similar construction to that of the back 330 of the exemplary strip 3100. The inner layer 3320 may be water proof or of limited permeability, and may not be of a foil like construction. In various embodiments, chambers 3330 may be longitudinal so as to channel the activating solution 350 (when added via the optional aperture 3340) to the entirety of the exothermic reactant in the bonnet 3300. However, the chambers 3330 may be of any configuration, as is according to design preference. An elastic band 3350 may also be utilized to secure the bonnet 3300 to the user's head.

It should be understood that outer layer 3310 and inner layer 3320 may be made of opposite materials than described above. That is, in some embodiments, it may be desirable to have the outer layer 3310 as the water proof/limited permeability layer and the inner layer 3320 as the permeable material. In some applications, it is contemplated that the user may reverse the "wearing" of the bonnet 3300 during mid-treatment to go from a dry heat treatment (impermeable layer being the inner layer) to a wet heat treatment (impermeable layer being the outer layer), or vice versus. Therefore, the user can be afforded either option, if so desired.

As apparent from the above description, it is possible to configure a bonnet 3300 that has both the inner layer and outer layer as impermeable layers (dry heat), whereas venting gases from the exothermic reaction can be channeled out through the solution entrance hole 3340, or other holes (not shown) to provide venting. Conversely, it is possible to configure a bonnet 3300 that has both the inner layer and outer layer as permeable layers (wet heat). A viable modification of such a bonnet 3300 would be to have different rates of permeability for the inner layer and outer layer, thus allowing different levels of wet heat to be applied to the user's head/hair.

Another modification is to allow the seals 3330 between chambers to be water/solution proof, so as to allow a user to selectively activate different chambers as desired.

Massage Implements

Further embodiments disclosed below address a need for massage implements that are maintained at a relatively constant elevated temperature for a significant duration of time. In one embodiment, an exothermic massage implement includes a heat conducting vessel having an inner chamber surrounded by a wall with an inner surface and an outer surface. A reactant is inside the inner chamber of the vessel. Combining the reactant with an activator causes an exothermic reaction that heats the wall and maintains the wall at a substantially constant elevated temperature for a duration of time.

In another embodiment, an exothermic massage implement includes a heat conducting artificial stone having an inner chamber surrounded by a wall with an inner surface and an outer surface. A powder mixture is contained inside the inner chamber of the vessel. This powder mixture includes at least reactant particles. When the powder mixture is combined with an activator, an exothermic gel is created. This exothermic gel heats the wall and maintains the wall at a substantially constant elevated temperature for a duration of time By use of a non-electrical or non-fossil fuel heating source, the embodiments herein can be considered as self-contained units, portable, and also disposable with minimal to no environmental consequence. With a regulated, controlled exothermic reaction, overheating can be avoided, as well as burns that occur from such overheating. As with most disposable items, the embodiments can be of limited or of single use, whereby complications arising from reuse can be obviated. Also, with limited or single use products, they are of smaller size than institutional products. Therefore, the exemplary embodiments can also be easily shipped, easily stored (e.g., suitcase, handbag, etc.), and are much more affordable for the individual user.

Figure 9:
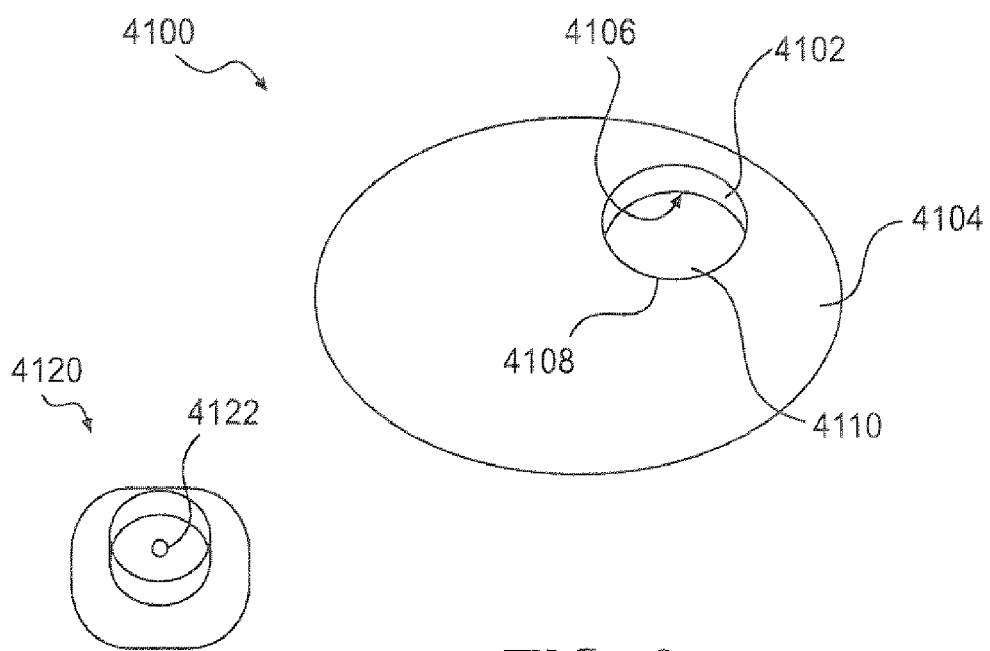
FIG. 9 is a perspective view of an exothermic massage implement.

An exothermic therapeutic massage implement is shown in FIG. 9. Massage implement 4100 is a hollow vessel and includes inner chamber 4110 which is surrounded by vessel wall 4102. Vessel wall 4102 has outer surface 4104 and inner surface 4106. Aperture 4108 provides communication between inner chamber 4110 and the ambient environment. Aperture 4108 may be covered by cap or plug 4120. Cap 4120 includes valve 4122, which is a small opening in cap 4120. In some embodiments, massage implement 4100 is aesthetically designed to resemble a natural stone.

Massage implement 4100, whether or not designed to resemble a stone, may be manufactured in a wide variety of shapes. Preferably massage implement 4100 has smoothly curved surfaces in multiple different contours so that the massage therapist can treat the massage recipient with different levels of pressure using the same implement 4100. For example, massage implement 4100 may have one side with a relatively small radius curved surface and another side with a larger radius curved surface. Pressing these different surfaces of massage implement 4100 against the massage recipient's body will provide the massage recipient with different sensations.

Figure 10:
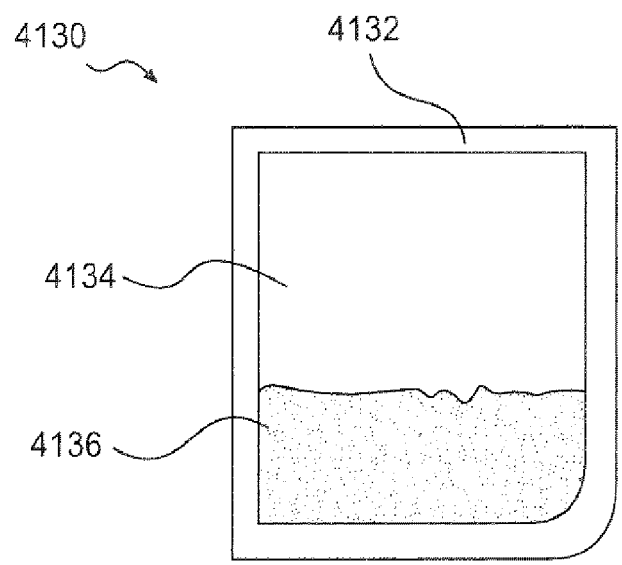
FIG. 10 is a front view of a pouch containing a powder mixture containing at least reactant particles.

FIG. 10 shows pouch 4130 which is contained within the inner chamber or inserted through aperture 4108 into inner chamber 4110 of massage implement 4100. Pouch 4130 includes internal container 4134 which is sealed about its periphery 4132. Powder mixture 4136 is contained inside internal container 4134. Powder mixture 4136 includes at least reactant particles. When the reactant particles are combined with an activator, an exothermic reaction occurs and heat is released. Pouch 4130 is permeable to the activator that reacts with the reactant particles. The activator may be a liquid or gas. Where the activator is water or a water-based solution, pouch 4130 is water permeable. The exothermic reaction is discussed in further detail elsewhere herein.

Figure 11:
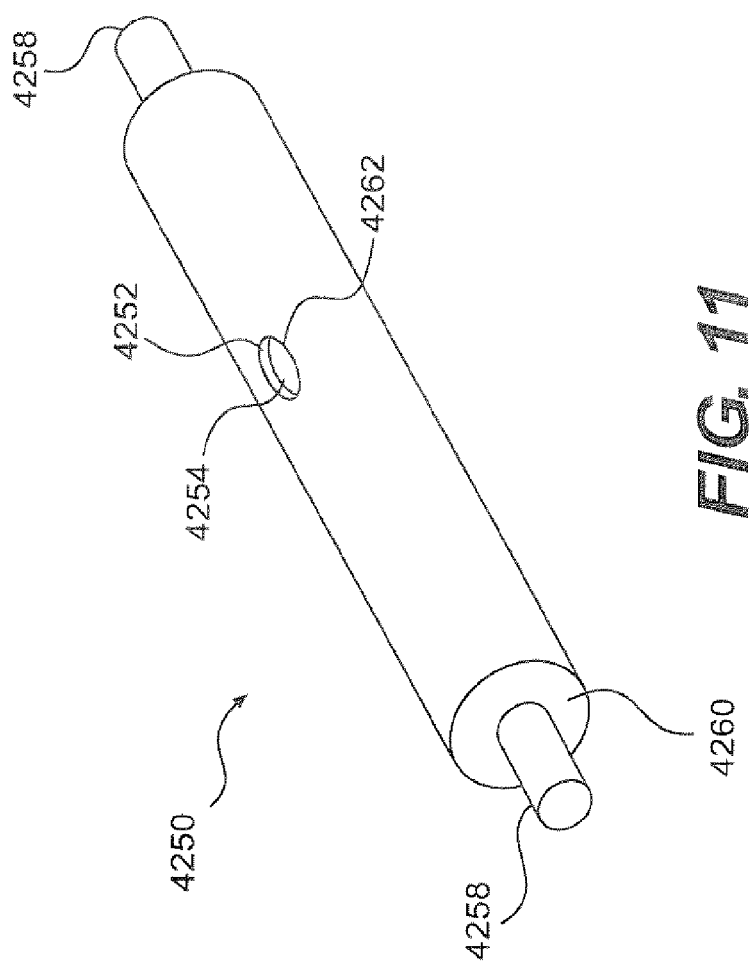
FIG. 11 is a perspective view of a rolling pin exothermic massage implement.

FIG. 11 shows an alternative embodiment of an exothermic therapeutic massage implement. Exothermic massage rolling pin 4250 is a hollow vessel and includes inner chamber 4254 surrounded by vessel wall 4252. Vessel wall 4252 is formed in the shape of a cylinder and includes flat end portions 4260 at each end of the cylinder. Handles 4258 are optionally attached to end portions 4260. Handles 4258 may be fixed relative to end portions 4260, or end portions 4260 and vessel wall 4252 may be rotatable relative to handles 4258. Vessel wall 4252 or end portions 4260 may incorporate an aperture, such as aperture 4262 shown in FIG. 11. As with the previously disclosed embodiment, pouch 4130 is contained inside inner chamber 4254.

Figure 12:
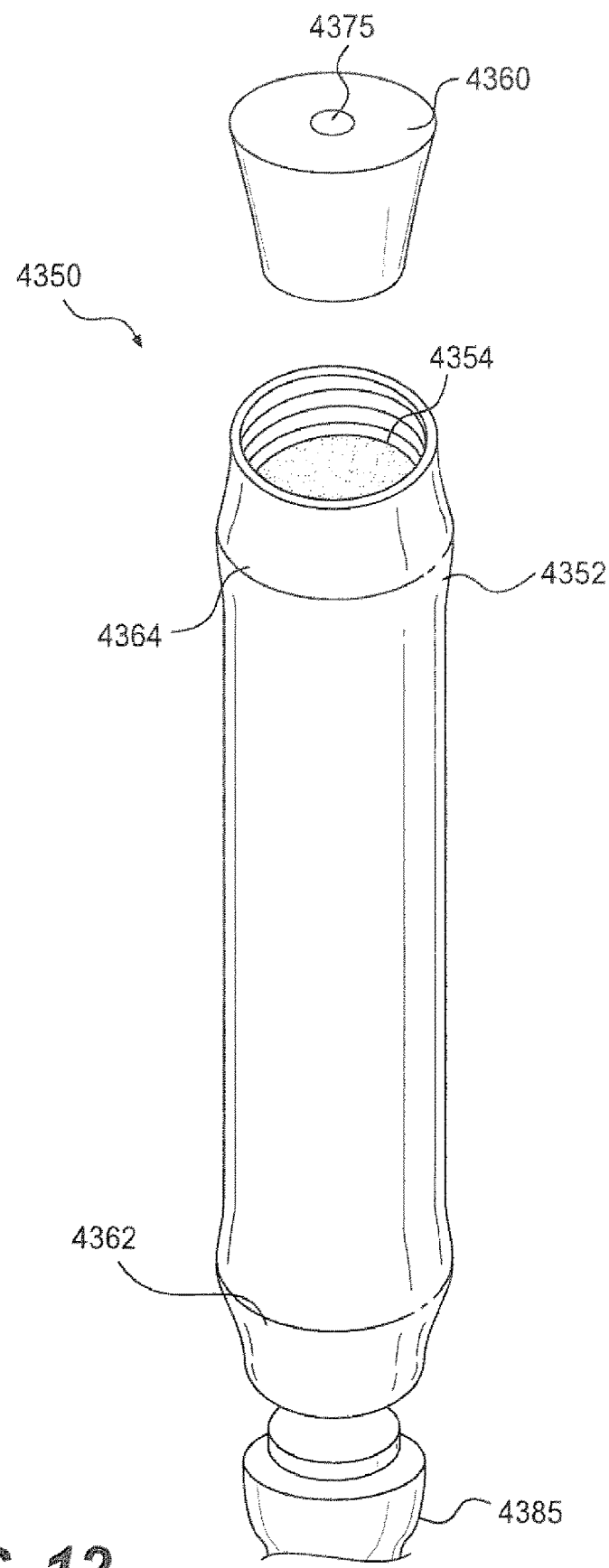
FIG. 12 is a perspective view of an alternative exothermic massage implement.

FIG. 12 shows another alternative embodiment of an exothermic therapeutic massage implement that may be constructed of bamboo. Exothermic massage implement 4350 is a hollow vessel and includes inner chamber 4354 surrounded by vessel wall 4352. Vessel wall 4352 is naturally formed in the shape of a cylinder and includes natural bulkhead 4362 and a drilled bulkhead 4364 at each end of the cylinder. A stopper 4360 with a vent hole 4375 may be fixed to an end of the cylinder. The stopper 4360 may be constructed from various materials, such as bamboo, plastic, or other woods such as Mediterranean oak. Additionally, a cap 4385 may be optionally attached to an end of the cylinder. The cap 4385 may be constructed of bamboo, other woods or various plastic materials, and may vary in shape, such as rounded or flat, depending on the therapeutic technique desired. The exothermic massage implement 4350 may be filled with powder mixture in the form of a tubular heating charge such as shown in FIGS. 13*a* to 13*c*.

Figure 13A:
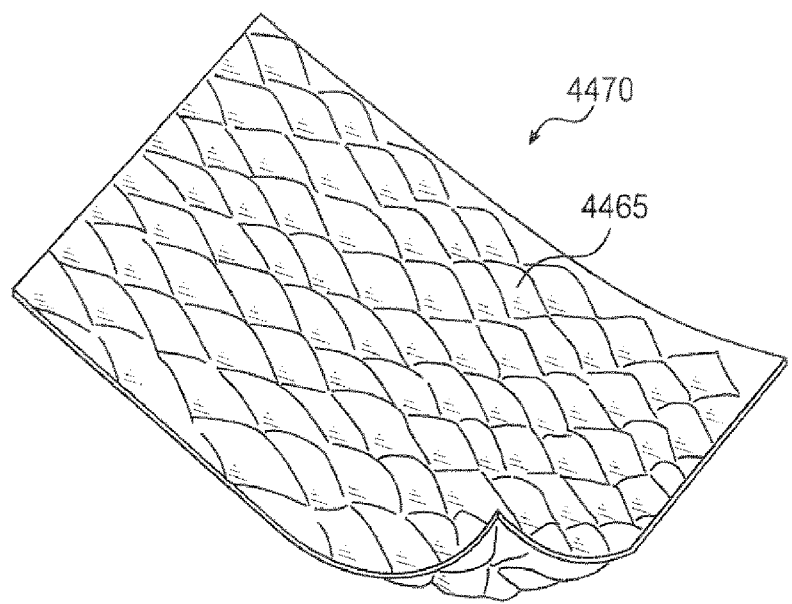
FIG. 13A is a perspective view of a sheet containing reactant.
Figure 13B:
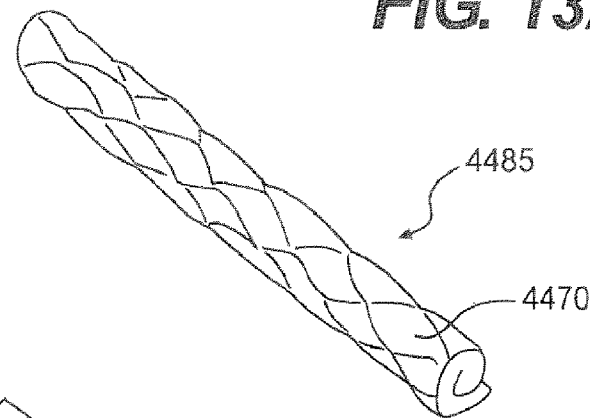
FIG. 13B is a perspective view of a tubular heating charge.
Figure 13C:
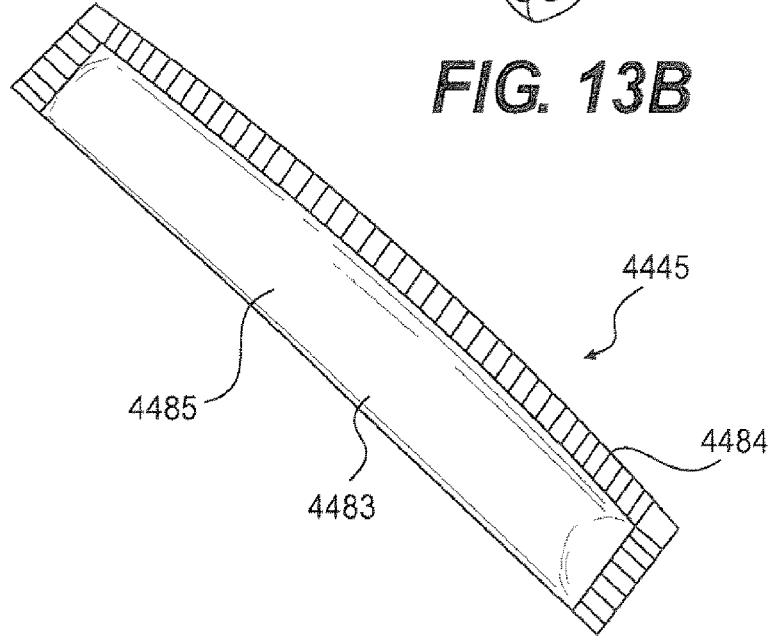
FIG. 13C is a perspective view of a sealed heating charge.

FIG. 13A shows a sheet 4470 constructed of non-woven plastic or another suitable material that contains an exothermic composition 4465 such as Lava Gel®. The exothermic composition 4465 may be affixed to the sheet 4470 by ultrasonic sealing or any suitable method as known in the art. FIG. 13B shows a tubular heating charge 4485 prepared by rolling a sheet 4470 into a tube shape. The diameter of the tubular heating charge 4485 may vary depending on the diameter of a massage implement. FIG. 13C shows a sealed heating charge 4445 prepared by packaging a tubular heating charge 4485 in a wrapper 4483. The wrapper may be constructed of a water soluble paper. The tubular heating charge 4485 may optionally be further sealed with a water soluble plastic film wrapper 4484. Prior to use, the sealed heating charge 4445 may be unwrapped, and the tubular heating charge 4485 placed in the inner chamber 4354 of a massage implement such as shown in FIG. 12.

Regardless of the massage implement used, powder mixture 4136 is placed inside its inner chamber, either directly, or inside pouch 4130. Prior to use of the massage implement, the reactant particles are kept separate from the activator. Once the activator is added to the reactant particles inside the inner chamber of the massage implement, an exothermic reaction occurs and heat is released and transferred to the vessel walls, primarily by conduction. This exothermic reaction thus heats the massage implement to an elevated temperature, and the massage implement is maintained at approximately this temperature until the heat releasing phase of the exothermic reaction ceases.

Powder mixture 4136 may also include salt particles. The salt particles may be sodium chloride, but other salts such as magnesium chloride may also be used. Alternatively, powder mixture 4136 may include no salt particles, in which case the water combined with powder mixture 4136 may contain dissolved salts. Although not illustrated, powder mixture 4136 may also include perfume particles that give off pleasing aromas when combined with water.

To use exothermic therapeutic massage implement 4100, a user places powder mixture 4136 (which may be inside water-permeable pouch 4130) into inner chamber 4110 of massage implement 4100. The user then adds a predetermined amount of activator to powder mixture 4136 inside inner chamber 4110 of massage implement 4100. Where the massage implement has aperture 4108 through which powder mixture 4136 was inserted into inner chamber 4110, activator is added to inner chamber 4110 through aperture 4108. After the activator is added, cap 4120 is placed over aperture 4108 so that powder mixture 4136 (optionally inside pouch 4130) cannot escape inner chamber 4110, though gas can escape through valve 4122 so as to prevent pressure buildup inside inner chamber 4110.

The user then allows the exothermic reaction between the reactant particles and the activator to take place so that heat is transferred to vessel wall 4102. Once massage implement 4100 reaches the desired elevated temperature (which may be anywhere from 98.6° F. to as hot as the massage recipient desires, for example 115°–120° F.), the user applies massage implement 4100 to the massage recipient. The user rubs massage implement 4100 on the massage recipient's body using the technique of a typical hot stone massage. Unlike a conventional hot stone massage, however, massage implement 4100 will remain at the relatively constant elevated temperature for a long duration of time, anywhere from 15 minutes to over 1 hour. If the user is using rolling pin massage implement 4250 to perform the massage, the user will roll heated rolling pin massage implement 4250 along the massage recipient's body.

Any of the massage implements disclosed above may be made from a wide variety of materials including ceramics, thermoplastic resins, glass, pottery, woods such as bamboo and other moldable heat conducting materials. The pouch containing the powder mixture likewise may be made from a wide variety of materials including woven and non-woven materials, paper, cellulose, natural fibers, polyethylene or polypropylene. The shape and size of the massage implements and pouch disclosed above may vary widely according to the design preferences of the user.

With respect to the above description, it is to be realized that the optimum dimensional relationships for the parts of the exemplary embodiments, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. It should also be appreciated that the exothermically heated apparatus of the present invention is suitable for usage in the application of various topical products and is not limited in its utility to the application of skin care or pain relief products.

Further, it is to be understood that the invention is capable of other embodiments and of being practiced and carried out in various ways. Also, it is to be understood that the invention is not limited in its application to the details of construction and that all matter herein described or shown in the accompanying drawings is to be interpreted as illustrative and not limiting.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A massage implement, comprising:
a heat conducting vessel having an inner chamber surrounded by a wall with an inner surface and an outer surface and at least one aperture, the vessel being elongated with opposing end portions, each end portions further comprising members extended away from the vessel, the vessel further comprising a cap engaged with the at least one aperture, the cap having a valve that sequesters the reactant and activator inside the inner chamber while allowing gas flow out of the inner chamber; and
a reactant comprising a powdered mixture contained within a liquid-permeable pouch formed by a liquid permeable membrane, wherein the liquid-permeable pouch is removably positioned inside the inner chamber of the vessel;
wherein a liquid activator is combined with the reactant by permeating the liquid-permeable pouch,
wherein an exothermic reaction is caused in the massage implement by intermixing the reactant and the liquid activator thereby heating the wall of the heat conducting vessel at a substantially constant elevated temperature.

2. The implement of claim 1, wherein the at least one aperture in the wall is disposed between the opposing end portions.

3. The implement of claim 1, wherein the outer surface of the wall includes at least two portions, each with a different texture.

4. The implement of claim 1, wherein the reactant comprises magnesium chloride and/or sodium chloride particles.

5. The implement of claim 1, wherein the reactant further comprises perfume particles so that the exothermic reaction produces a fragrant odor.

6. The implement of claim 1, wherein combining the liquid activator with the reactant forms an exothermic gel.

7. The implement of claim 1, wherein the at least one aperture is formed in one of the opposed end portions.

8. The implement of claim 1, wherein the heat conducting vessel is constructed from stone, ceramic, resin, glass, or wood.

9. The implement of claim 1, wherein at least a portion of the outer surface of the wall has a smooth texture.

10. The implement of claim 1, wherein the heat conducting vessel is constructed from bamboo.

11. The implement of claim 1, wherein the duration of time is between approximately 15 minutes and 1 hour.

12. The implement of claim 1, wherein the permeable membrane of the liquid-permeable pouch is constructed from woven or non-woven materials, paper, cellulose, natural fibers, polyethylene, or polypropylene.

13. The implement of claim 1, wherein the outer surface of the wall includes at least two portions, each with a different radius of curvature.

* * * * *